Figure 1:
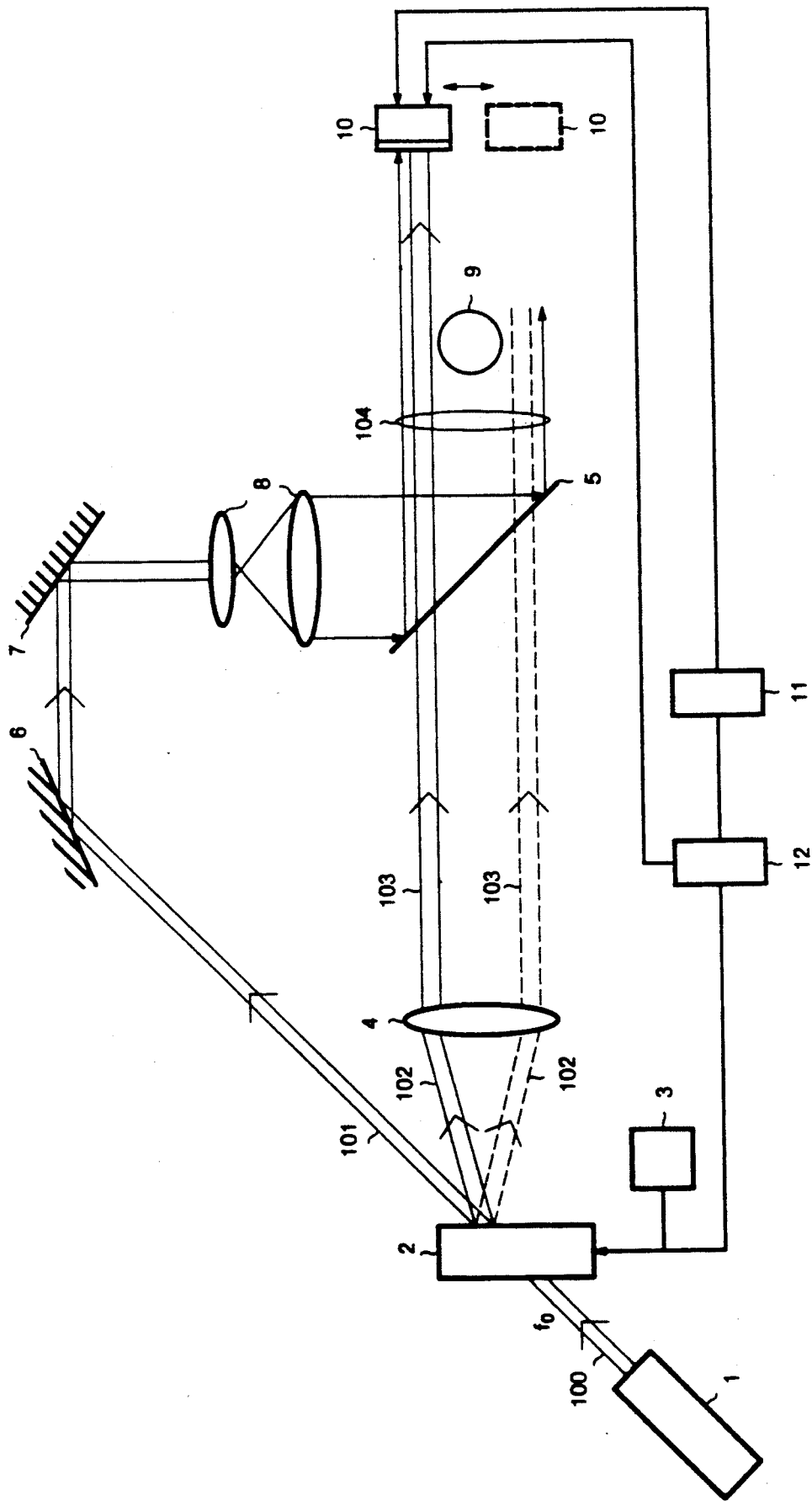

United States Patent [19]

Cocito et al.

[11] Patent Number: 5,160,973
[45] Date of Patent: Nov. 3, 1992

[54] SYSTEM FOR MEASURING THE REFRACTIVE INDEX PROFILE OF OPTICAL COMPONENTS

[75] Inventors: Giuseppe Cocito, S. Giusto; Giorgio Greco, Venaria, both of Italy

[73] Assignee: CSELT - Centro Studi E Laboratori Telecomunicazioni S.p.A., Turin, Italy

[21] Appl. No.: 778,740

[22] Filed: Oct. 18, 1991

[30] Foreign Application Priority Data

Oct. 22, 1990 [IT] Italy .................. 67814 A/90

[51] Int. Cl.$^5$ .............................. G01N 21/45
[52] U.S. Cl. ...................... 356/73.1; 356/128; 356/349; 356/361
[58] Field of Search .............. 356/73.1, 349, 361, 356/128

[56] References Cited

U.S. PATENT DOCUMENTS 5,089,698  2/1992  Grego .................. 356/349 X

Primary Examiner—Vincent P. McGraw
Attorney, Agent, or Firm—Herbert Dubno

[57] ABSTRACT

The system uses a monochromatic radiation source (1) and an acousto-optic modulator (2), which is driven by a periodically variable frequency. The modulator emits a first beam having the same wavelength as the source and a second beam, whose wavelength and emission direction vary with the modulating frequency. After the second beam has been collimated, radiations of both beams are sent towards the component under test and an electrical signal with varying frequency is generated representative of the beat between such radiations at the output from the component. A spectral analysis of the beat signal is carried out, and the refractive index value is derived from the position taken by the various frequencies of the beat signal on a detection plane.

9 Claims, 2 Drawing Sheets

SYSTEM FOR MEASURING THE REFRACTIVE INDEX PROFILE OF OPTICAL COMPONENTS

DESCRIPTION

The present invention relates to a method of and an apparatus for determining the refractive index profile of optical components. Preferably but not exclusively the invention is applied to the determination of the refractive index profile of optical fibres or optical fibre preforms.

The refractive index profile of optical fibres plays an essential role in determining a number of important fibre characteristics, e.g. light collection efficiency, guiding properties and bandwidth. It is important to know this profile already during fabrication of the fibre, since in this way interventions can be made to correct possible anomalies found out. E.g., the measurement can be made on the preform, whose refractive index characteristics are the same as in the resulting fibre, and which yet has a much greater diameter and is then easier to handle. Of course refractive index measurement for controlling the production must be effected with non-destructive methods, i.e. methods which do not require cutting away a sample of the fibre under test.

Various non-destructive methods of determining the refractive index profile of optical fibres and optical fibre preforms have already been suggested and, among them, those based on interferometric techniques are of particular interest, since they allow measures independent of possible power fluctuations of the sources.

An example of interferometric system is described in EP-B 0 085 981 in the name of the Applicant. In this known system, a light beam comprising two slightly different frequencies is generated, this beam is split into the two component radiations, one of the two radiations is sent along a path which intersects the fibre or preform and the other along a path which does not intersects the fibre, electrical signals are generated representative of the beats between the two radiations and the refractive index profile is derived from the phase difference between said beats and a reference beat obtained from the two component radiations which have both followed a path external to the fibre or preform. Such a system can be used to determine the refractive index of whatever optical component.

This known system presents a number of disadvantages due to the fact that the phase differences between two signals are analyzed. More particularly phase differences greater than $2\pi$ cannot be determined, unless a measurement is made of a relative phase shift with respect to a reference body, such that the differences between the phase shifts introduced by the body under test and by the reference body are lower than $2\pi$. The presence of a reference body renders the system complicated. Besides it is necessary to ensure that the measurement beat and the reference beat have exactly the same frequency.

The disadvantages of the prior art are overcome by the system of the present invention which exploits a variable frequency beat and its spectral analysis.

From italian patent application No. 67516-A/89 filed on Jun. 27, 1989 in the name of the Applicant, a system for measuring displacements of a moving device is already known, wherein a beat is generated of which the frequency is variable in function of the device position and the difference is measured between the frequency of said beat in a current position and in a reference position of the device. For measuring angular displacements, the moving device is integral with a transparent body (e.g. a plate with parallel and plane faces) which, in an embodiment of the system, is placed on the path of the beam from which the variable frequency beat is derived. However, in this known system, the transparent body characteristics, and more particularly its refractive index, must be known a-priori, whilst the aim of the present invention is just that of determining such characteristics.

According to the invention there is provided a method of measuring the refractive index profile of an optical component, wherein: a first basically monochromatic light beam at a first frequency is generated; a second and a third basically monochromatic beams are obtained from the first beam, the second beam having the same frequency as the first beam, and the third beam having a variable frequency which is at any instant different from the first frequency, being emitted in a direction varying in function of the frequency and being then collimated; radiations of the second beam and of the collimated third beam are sent towards the optical component; an electrical signal is generated at said varying frequency, representative of the beat among the radiations which have passed through the optical component; and a spectral analysis of this electric signal is carried out, and wherein the radiations which have passed through the optical component are collected on a detection plane located at a constant and predetermined distance from the optical component, the position taken by each spectral component of such signal in said detection plane is determined and the refractive index profile is derived from the distance between said position and that taken by the same spectral component in the absence of optical component.

The invention also provides an apparatus for implementing the method, comprising:

a source of monochromatic light emitting a first beam at a first wavelength;

an acousto-optical modulator, operated as a Bragg modulator and driven by an electrical signal with periodically varying frequency, for obtaining from the first light beam a second beam, having the same wavelength as the first, and a third beam having variable frequency and direction, which is collimated;

means for sending into the component under test radiations from the second beam and from the collimated third beam; and means for collecting radiations of the second and third beams outgoing from the component, for generating a variable frequency electrical signal representative of the beat among said radiations, for making a spectral analysis and for processing the analysis results;

wherein said collecting, generating, analysing and processing means, are arranged to collect the radiations outgoing from the optical component on a detection plane at a predetermined and constant distance from the component, to detect the position assumed by each spectral component of the signal on the detection plane in the absence of the optical component and to derive the refractive index profile starting from the displacement undergone by the individual spectral components as an effect of passing through the optical component.

Figure 2:
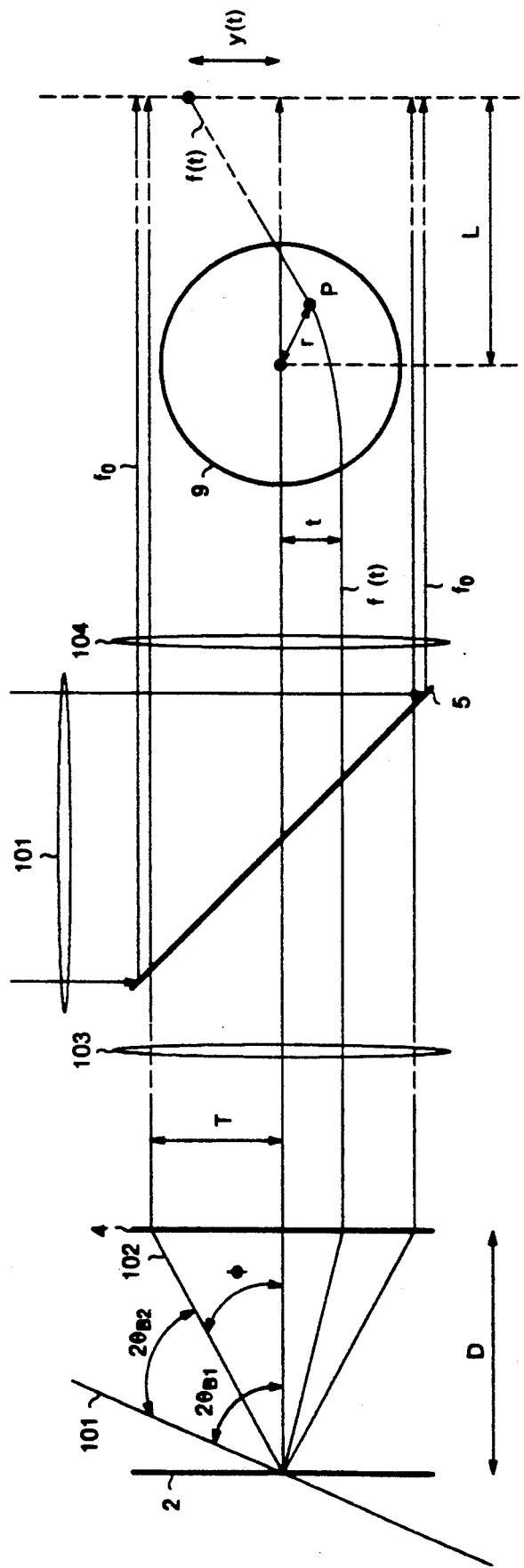

For a better understanding reference is made to the annexed drawing, wherein:

FIG. 1 is a schematic representation of the apparatus in accordance with the invention; and FIG. 2 is a simplified and enlarged diagram of part of the apparatus of FIG. 1.

Referring to the drawings, a light beam 100 generated by a substantially monochromatic source, e.g. a laser 1 operating at a frequency $f_0$, is applied to an acousto-optic cell 2 driven by an electrical signal with a variable frequency and operating as a Bragg type modulator: in other words, the light beam 100 is applied to the acousto-optic cell 2 with an incidence angle equal to Bragg angle $\theta_B$, which as known, depends on wavelength $\lambda$ of the optical signal and wavelength $\Lambda$ of the acoustic signal induced by the electrical signal, according to relation $\sin\theta_B = \lambda/2\Lambda$.

Driving a cell with a variable frequency electrical signal is well known in the art and cells driven by a signal whose frequency may vary from some MHz to about one GHz are commercially available. Preferably the electrical signal is obtained by frequency modulating the radiofrequency signal generated by an oscillator by means of a saw-tooth signal, whose frequency is much lower than that of the oscillator signal (e.g. a frequency in the order of some kHz). Reference 3 denotes the generator of the signal at variable frequency F for driving cell 2. This frequency F is supposed to vary around a central value $f_1$ between two extreme values $f_1 - f_2$, $f_1 + f_2$.

Under the above conditions the acousto-optic cell emits a non-deflected beam 101, at the same frequency $f_0$ as the beam emitted by laser 1, and a beam 102, deflected by twice the Bragg angle from beam 101, and having a frequency which differs from frequency $f_0$ by the modulating frequency. By way of example, beam 102 is supposed to have a frequency $f_0 + F$. Since the modulating frequency F is variable, both the emission angle and the frequency of deflected beam 102 will also vary from instant to instant; more particularly, if $\theta_{B1}$, $\theta_{B2}$ (FIG. 2) denote the Bragg angles corresponding to central frequency $f_1$ and to one of the extreme frequencies of the modulation range (e.g. minimum frequency $f_1 - f_2$), the deflected beam will move through an angle $2\phi$, where $\phi = 2(\theta_{B1} - \theta_{B2})$, during a period of the saw-tooth signal. A different frequency value will characterize each position within the angular range $2\phi$.

Deflected beam 102 is collimated by an optical system which is placed at its focal distance from the exit face of cell 2 and is of a size allowing it to encompass the whole angle $2\phi$; in this way whatever the emission angle of beam 102, a beam is obtained which always propagates in the same direction. Radiations with frequency $f_0 + f_1$ (corresponding to the central frequency of the frequency range of deflected beam 102) will propagate along the axis of optical system 4 and, if D is the focal length of optical system 4, the positions corresponding to the two extreme frequencies $(f_0 + f_1 + f_2, f_0 + f_1 - f_2)$ will be spaced apart by a distance $2T = 2D \cdot \tan\phi$. In other words, for each unit variation of the modulating signal frequency, collimated beam 103 will undergo a displacement, perpendicular to the axis of optical system 4, given by $$\tau = D \cdot \tan\phi / f_2 \quad (1)$$

FIG. 1 shows trajectories corresponding to the two extreme frequencies at the output of optical system 4. The angles have been enhanced to make the drawing clearer. Beams 100, 101, 102, 103 are shown with finite-size cross section to indicate that, owing to the linewidth of source 1, each of them comprises a certain frequency range. Also beam widths have been enhanced.

A beam recombiner 5, in practice a semi-transparent mirror, is placed in the path of collimated beam 103. It is traversed by that beam and it also receives, on its reflecting face, beam 101 at frequency $f_0$ from acousto-optic cell 2. Beam 101 reaches semi-transparent mirror 5 via mirrors 6, 7. Its cross-sectional size is appropriately expanded to a diameter at least equal to distance 2T between the extreme positions of beam 103 by a beam expander schematized by lenses 8. In this way, whatever the position of beam 103, beam recombiner 5 generates a beam 104 which comprises both radiations at frequency $f_0$ and radiations at frequency $f_0 + F$ and which is sent to optical component 9 (e.g. an optical fibre or an optical fibre preform) whose refractive index profile is to be determined. Radiations at frequency $f_0 + F$ have within beam 104 a position which is a function of the value of F.

Recombined beam 104 is refracted by optical component 9 depending on the incidence angle (and hence on the distance from the axis) and on the refractive index profile of the component. The refracted beam is then collected by a photodetector 10, e.g. a photodiode, which is associated with a motor controlling its displacements so that the detector scans the refracted beam at a much lower speed than the refracted beam displacement speed. The detector can thus be considered as basically stationary with respect to this beam. Detector 10 generates an electrical beat signal between the radiations which form the portion of refracted beam it intercepts. This electrical signal has variable frequency F depending on the position of detector 10, since each incidence point of beam 104 on optical component 9 corresponds to a different value of the frequency of the incident radiation coming from beam 103. In practice, by neglecting for sake of simplicity the source linewidth, owing to the non-null size of the detector, a certain range $\Delta F$ of the frequencies present in beam 104 and coming from beam 103 will take part in beat generation: since the different frequencies in in this range are emitted at different instants, the beat frequency will have a time-variable frequency even for a given position of the detector.

Photodetector 10 is connected to a frequency measurement device 11 which, for each position of the detector, measures the average beat frequency in a measurement interval of suitable duration (e.g. 1 s). Device 11 can be e.g. a counter which counts the average number of pulses generated by the photodetector; measurement device 11 is then followed by a processor 12, which derives the refractive index from the beat frequency value. Processor 12 can also control the photodetector displacement.

In the particular application to a graded index optical fibre or optical fibre preform, supposing that the fibre or preform is immersed in an index matching fluid and considering a ray which propagates parallel to the optical system axis and which arrives on the fibre or preform 9 at a point at distance t from the axis (FIG. 2), the refracted ray reaches an observation plane (in this case the plane of the sensing surface of detector 10), placed at distance L from the fibre centre, at a point placed at a distance y(t) from the axis. If $n_2$ is the refractive index of the fibre cladding, refractive index n(r) at a point P inside the fibre, at a distance r from the axis, is given by the well known relation $$n(r) - n_2 = \frac{n_2}{\pi L} \int_r^\infty \frac{y(t) - t}{(t^2 - r^2)^{\frac{1}{2}}} \quad (2)$$

The way in which this relation is obtained is described e.g. in "Principles of Optical Fiber Measurements", by D. Marcuse, Academic Press 1981, par. 4.6 and 4.7.

Owing to the way in which the beam sent towards the fibre or preform is generated, each value of t, and then each value of y, corresponds to a certain average frequency f(t) of the heat. Measurement device 11 supplies processing device 12 with the average frequency value detected; processing device carries out the mathematical computations according to relation (2). The position y(t) of the detector is easy to determine, e.g. by shifting the detector along a graded guide, or it can be already known to the processing device, if the detector movement is controlled by it. Value t is also known to the processing device where, in an initialisation phase during which the detector collects the recombined signal in the absence of fibre or preform 9, a table associating the different values of the beat frequency with the corresponding values of t, with the desired resolution, is generated using relation (1).

We will make now some remarks permitting evaluation of the performance of the invention. In case of an optical fibre, it is to be taken into account that the core diameter is of the order of some tens micrometers (e.g. 30 μm). To obtain a precise profile, scanning could be carried out in steps of a fraction of a micrometer, e.g. 0.5 μm.

Obtaining controlled displacements of detector 10 in steps of this magnitude is not a problem, since commercially available motors for applications in the domain of optical measurements permit displacements in steps even of the order of some nanometers.

In order to perform the invention, acousto-optical cell 2 can be a commercially available cell modulated by a 150±50 MHz frequency, so that $f_2 = 50$ MHz; since the whole of the core and cladding of a fibre for telecommunications has a diameter of 125 μm, the focal distance D of optical system 4 can be chosen so that shift T of the beam corresponding to a modulation frequency variation by 50 MHz is 0.5 mm (500 μm); under these conditions the beam sent towards the fibre is no doubt completely external to the fibre in the extreme positions and is totally within the fibre in the axial position. With a cell and an optical system of these characteristics, τ is 10 μm/MHz. In order to measure detector displacements (and hence variations of y) of the order of 0.5 μm, a frequency variation of the order of some ten kHz must be measured in a signal whose maximum frequency attains 200 MHz. That measurement precision can be obtained by commercially available and relatively cheap counters, by which frequencies of the order of hundreds of MHz can be measured with a precision of the order of a hundred Hz (and hence a precision 100 times higher than that required). Moreover, a cell with the characteristics above is neither particularly sophisticated nor expensive.

If the refractive index profile of a preform instead of that of a fibre must be measured, it is to be taken into account that the diameter is about 100 times greater than that of the fibre (e.g. 16 mm instead of 125 μm) and hence a lens with much higher focal length is to be chosen in order that the recombined beam encompasses the whole preform: e.g., focal length D can be chosen so that T=10 mm. Using the same cell as above, τ is now 0.2 mm/MHz and, if a counter with the characteristics mentioned above is used for frequency measurement, a scanning in steps of some micrometers can be carried out, thus obtaining a set of points which is surely sufficient for characterizing the component.

Of course, the more sophisticated the frequency measurement device 11, the higher the resolution with which the profile may be determined. Besides, for a given device, the higher the bandwidth of the collected signal, the higher the resolution. It can be stated that theoretically no lower limit to sensitivity exists for an apparatus according to the invention, apart from the limits imposed by the linewidth of the electronic oscillator which controls modulator 2; the lack of precision inherent in such linewidth can be compensated by making repeated measurements and averaging the results.

The above embodiment has been described only by way of non-limiting example; variations and modifications are possible without departing from the scope of the invention. In particular a photodetector comprising a matrix of sensing elements and having such a size as to intercept the whole refracted beam can be used in place of moving photodetector 10: measurement device 11 will hence receive signals with different frequencies from the different detector elements. This solution allows to eliminate moving devices, but it gives only a profile by points, whilst in the preceding case a substantially continuous profile can be obtained. It is to be also noted that a component with basically constant refractive index would not require scanning.

Moreover, even if explicit reference has been made to refractive index profile measurement, it is clear that the operating principle can be applied to determine those characteristics which affect the optical path of a light beam inside an optical component: hence not only the refractive index, but also the geometric shape of a body of known refractive index, etc., can be determined.

We claim:

1. A method of measuring the refractive index profile of an optical component (9), wherein: a first basically monochromatic light beam (100) is generated comprising radiations at a first frequency; a second and a third basically monochromatic beam (101, 102) are obtained from the first beam, the second beam having the same frequency as the first beam, and the third beam having a variable frequency different at any instant from the first frequency, being emitted in a direction varying in function of the frequency and being then collimated; radiations of the second beam (101) and of the collimated third beam (103), are sent towards the optical component (9); an electrical signal at said variable frequency is generated, representative of the beat between radiations which have passed through the optical component (9); and a spectral analysis of the electrical signal is carried out; characterized in that the radiations which have passed through the optical component (9) are collected on a detection plane located at constant and predetermined distance from the optical component (9), the positions taken by the individual spectral components of such signal in said detection plane are determined and the refractive index profile is derived from the distance between each said position and that taken by the same spectral component in the absence of the optical component.

2. A method in accordance with claim 1, characterized in that for said spectral analysis a scanning of the beam outgoing from the optical component is effected in said detection plane by a detector (10).

3. A method in accordance with claim 1, characterized in that for said spectral analysis a detector comprising a matrix of sensing elements is arranged in said detection plane, which matrix has such a size as to encompass all the possible arrival positions in said plane of the radiations which have passed through the component under test.

4. A method according to claim 1, characterized in that said optical component is an optical fibre or an optical-fibre preform.

5. A method for determining the characteristics of an optical component (9) which affect the optical path of light radiations inside the component wherein a first basically monochromatic light beam (100) is generated comprising radiations at a first frequency; a second and a third basically monochromatic beams (101, 102) are obtained from the first beam, the second beam having the same frequency as the first beam, and the third beam having a variable frequency different at any instant from the first frequency, being emitted in a direction varying in function of the frequency and being then collimated; radiations of the second beam (101) and of the collimated third beam (103) are sent towards the optical component (9); an electrical signal at said variable frequency is generated, representative of the beat among radiations which have passed through the optical component (9); and a spectral analysis of the electrical signal is carried out; characterized in that the radiations which have passed through the optical component (9) are collected on a detection plane located at constant and predetermined distance from the optical component (9), the positions taken by the individual spectral components of such signal in said detection plane are determined and the desired characteristics is derived from the distance between each said position and that taken by the same spectral component in the absence of the optical component.

6. A system for measuring the refractive index profile of an optical component, comprising:
 a source of monochromatic light (1) emitting a first beam (100) at a first wavelength;
 an acousto-optical modulator (2), operated as a Bragg modulator, which is driven by an electrical signal with periodically varying frequency, for obtaining from the first light beam (100) a second beam (101), having the same wavelength as the first, and a third beam (102) having variable wavelength and direction, which is collimated;
 means for sending into the optical component under test radiations from the second beam (101) and from the collimated third beam (103); and
 means (10,11,12) for collecting radiations of the second and third beams (101, 103) outgoing from the component, for generating a variable frequency electrical signal representative of the beat among said radiations, for making a spectral analysis of the electrical signal and for processing the analysis results,
characterized in that said collecting, generating, analysing and processing means (10,11,12) are arranged to collect the radiations outgoing from the optical component onto a detection plane located at a predetermined and constant distance (L) from the optical component, to detect the position assumed by each spectral component of the signal on the detection plane, to detect the position of each spectral component on the detection plane in the absence of the optical component (9) and to obtain the refractive index profile from the displacement undergone by the individual spectral components as an effect of traversing the optical component.

7. A system according to claim 6, characterized in that said analysing means (10) comprises a photodetector placed in said detection plane, which periodically scans the light beam outgoing from the optical component (9), with a scanning period much higher than the period of variation of the driving frequency of the modulator (2).

8. A system according to claim 6, characterized in that said analysing means comprises a matrix of photosensitive elements placed in said detection plane and having a size enabling it to intercept the beam outgoing from the component, whatever the position of the radiations composing said beam.

9. A system for measuring the characteristics of an optical component (9) which influence the optical path of light radiations inside the component, comprising:
 a source of monochromatic light (1) emitting a first beam (100) at a first wavelength;
 an acousto-optical modulator (2), operated as a Bragg modulator, which is driven by an electrical signal with periodically varying frequency, for obtaining from the first light beam (100) a second beam (101), having the same wavelength as the first, and a third beam (102) having variable wavelength and direction, which is collimated;
 means for sending into the optical component under test radiations from the second beam (101) and from the collimated third beam (103); and
 means (10,11,12) for collecting radiations of the second and third beams (101, 103) outgoing from the component, for generating a variable frequency electrical signal representative of the beat among said radiations, for making a spectral analysis of the electrical signal and for processing the analysis results,
characterized in that said collecting, generating, analysing and processing means (10,11,12) are arranged to collect the radiations traversing the optical component onto a detection plane located at a predetermined and constant distance (L) from the component, to detect the position assumed by each spectral component of the signal on the detection plane, to detect the position of each spectral component on the detection plane in the absence of the optical component (9) and to obtain the desired characteristics from the displacement undergone by the individual spectral components as an effect of traversing the optical component.

* * * * *